United States Patent [19]

Chai et al.

[11] 4,055,553

[45] Oct. 25, 1977

[54] (GLY$_3$-ALA)$^1$-SOMATOSTATIN

[75] Inventors: Sie-Yearl Chai, Royersford; John P. Yardley, King of Prussia, both of Pa.

[73] Assignee: American Home Products Corporation, New York, N.Y.

[21] Appl. No.: 609,254

[22] Filed: Sept. 2, 1975

[51] Int. Cl.$^2$ ............... C07C 103/52; A61K 37/00
[52] U.S. Cl. ........................ 260/112.5 S; 424/177
[58] Field of Search ............... 260/112.5 S; 424/177

[56] References Cited

U.S. PATENT DOCUMENTS

| 3,904,594 | 9/1975 | Guillemin et al. | 260/112.5 S |
| 3,931,140 | 1/1976 | Sarantakis | 260/112.5 S |

Primary Examiner—Delbert R. Phillips
Attorney, Agent, or Firm—Richard K. Jackson

[57] ABSTRACT

The growth hormone release inhibiting compound:

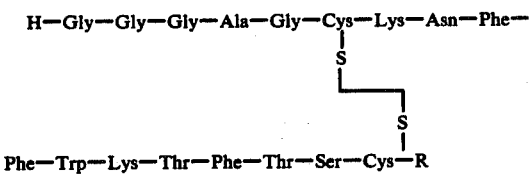

in which R is hydroxyl, dimethylamino, alkylamino of 1-5 carbon atoms or phenethylamine, the protamine zinc, protamine aluminum and non-toxic acid addition salts thereof as well as the corresponding linear heptadecapeptide and intermediates therefore are herein described.

3 Claims, No Drawings

(GLY₃-ALA)¹-SOMATOSTATIN

BACKGROUND OF THE INVENTION

The structure of the growth hormone release inhibiting factor, somatostatin, has been determined by Brazeau et al., Science, 179, 77(1973). Several techniques for synthesizing somatostatin have been reported in the literature, including the solid phase method of Rivier, J.A.C.S. 96, 2986(1974) and the solution methods of Sarantakis et al., Biochemical Biophysical Research Communications 54, 234(1973) and Immer et al., Helv. Chim. Acta, 57, 730(1974).

DESCRIPTION OF THE INVENTION

In accordance with this invention, there is provided a growth hormone release inhibiting compound of the formula; (Gly₃—Ala)¹-Somatostatin, and simple amides thereof as well as the non-cyclic form of the heptadecapeptide, the protamine zinc and protamine aluminum adducts, non-toxic acid addition salts thereof, and protected intermediates useful for the synthesis of the heptadecapeptide. The heptadecapeptides of this invention are useful in the treatment of conditions characterized by excessive growth hormone production, such as diabetes mellitus and acromegaly.

The heptadecapeptides of this invention present the amino acid sequence:

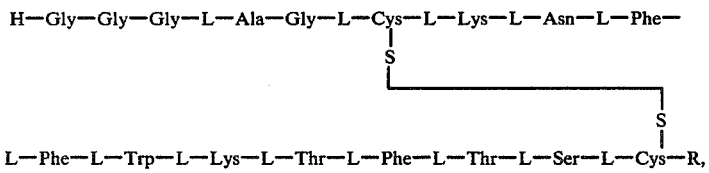

in the [6-17] cyclic form and are devoid of the disulfide linkage in the linear form, the group R representing hydroxyl, dimethylamino alkylamino of 1–5 carbon atoms or phenethylamino. The protamine zinc and protamine aluminum derivatives of the heptadecapeptide represent derivatives conventionally derived from polypeptides for characterization and administrative purposes. The acid addition salts of the heptadecapeptide are derived from both inorganic and organic acids known to afford pharmaceutically acceptable non-toxic addition products, such as hydrochloric, hydrobromic, sulfuric, phosphoric, maleic, acetic, citric, benzoic, succinic, malic, ascorbic acid and the like.

The heptadecapeptides of this invention are prepared by solid phase methodology, employing as the initial reactant the fully protected peptidoresin R¹-Ala-Gly-Cys (R²)-Lys (R³)-Asn-Phe-Phe-Trp-Lys (R⁴)-Thr(R⁵)-Phe-Thr (R⁶)-Ser (R⁷)-Cys (R⁸)-O-Resin, in which each of the protective R groups are defined, infra. Deprotection of the α-amino protecting group (R¹) of the alanyl moiety followed by the sequential coupling and deprotection of two glycyl moieties followed by the introduction of the terminal glycyl group affords the fully protected intermediate R¹-Gly-Gly-Gly-Ala-Gly-Cys (R²)-Lys (R³)-Asn-Phe-Phe-Trp-Lys (R⁴)-Thr (R⁵)-Phe-Thr (R⁶)-Ser (R⁷)-Cys (R⁸)-O-Resin, which is totally deprotected and removed from the Resin support by treatment with liquid hydrofluoric acid in the presence of anisole to yield the linear heptadecapeptide H-Gly-Gly-Gly-L-Ala-Gly-L-Cys-L-Lys-L-Asn-L-Phe-L-Phe-L-Trp-L-Lys-L-Thr-L-Phe-L-Thr-L-Ser-L-Cys-OH. If desired, the fully protected heptadecapeptide may be removed from the Resin support by aminolysis employing dimethylamine, methylamine, ethylamine, n-propylamine, i-propylamine, butylamine, iso-butylamine, pentylamine, or phenethylamine, to yield the 17-Cysteine amide of the fully protected linear heptadecapeptide. The protecting groups may then be removed by treatment with liquid HF in the presence of anisole or by catalytic (e.g. Pd on BaSO₄) hydrogenation under conditions avoiding attack of the tryptophan moiety.

The deprotected linear heptadecapeptide and the corresponding amides are readily converted to the [6-17] cyclic disulfide (H-Gly-Gly-Gly-Ala)¹-Somatostatin derivative by mild oxidation (e.g. air), preferably through exposure of a solution of the linear compound to atmospheric oxygen. The protamine zinc and protamine aluminum complexes and non-toxic acid addition salts are produced by methods conventional in the polypeptide art.

Thus the intermediates which constitute part of this invention may be represented as:

R¹-Gly-Gly-Gly-Ala-Gly-Cys (R²)-Lys (R³)-Asn-Phe-Phe-Trp-Lys- (R⁴)-Thr (R⁵)-Phe-Thr (R⁶)-Ser (R⁷)-Cys (R⁸)-X, in which X represents —OH, dimethylamine, alkylamino of 1 to 5 carbon atoms, phenethylamine or O—CH₂ -[polystyrene resin support]; in which:

R¹ represents hydrogen or an α-amino protecting group;

R² and R⁸ are protecting groups for the sulfhydryl group of the two cysteinyl moieties, independently selected from the group consisting of 3,4-dimethylbenzyl and p-methoxy-benzyl;

R³ and R⁴ are protecting groups for the epsilon amino group of the two lysyl moieties selected from benzyloxycarbonyl, 2-chloro benzyloxycarbonyl and 4-nitrobenzyloxycarbonyl;

R⁵, R⁶ and R⁷ are benzyl.

The α-amino protecting group represented by R¹ may be any group known in the art to be useful in the stepwise synthesis of polypeptides. The preferred α-amino protecting group defined by R¹ is of the urethane type and in particular tert-butyloxycarbonyl.

The criterion for selecting protecting groups for R²⁻⁸ are (a) the protecting group must be stable to the reagent and under the reaction conditions selected for removing the α-amino protecting group at each step of the synthesis, (b) the protecting group must retain its protecting properties (i.e. not be split off under coupling condition), and (c) the side chain protecting group must be removable upon the completion of the synthesis of the desired amino acid sequence, under reaction conditions that will not alter the peptide chain.

The group —O—CH₂-[polystyrene resin support] defining X in the intermediates of this invention described supra, represents the ester moiety of one of the many functional groups of the polystyrene resin support.

The solid phase method of preparing the heptadecapeptides of this invention is generally known in the art and is described by Merrifield, J.A.C.S., 85, 2149(1963). The resin support employed may be any suitable resin conventionally employed in the art for the solid phase preparation of polypeptides, preferably polystyrene which has been cross-linked with from 0.5 to about 3 percent divinyl benzene, which has been either chloromethylated or hydroxymethylated to provide sites for ester formation with the initially introduced α-amino protected amino acid.

The α-amino and sulfhydryl protected cysteine is coupled to the chloromethylated resin according to the procedure of Gisin, Helv. Chim. Acta., 56, 1476 (1973). Following the coupling of the α-amino and sulfhydryl protected cysteine to the resin support, the α-amino protecting group is removed by standard methods employing trifluoroacetic acid in methylene chloride, trifluoroacetic acid alone or HCl in dioxane. The deprotection is carried out at a temperature between about 0° C. and room temperature. After removal of the α-amino protecting group the remaining α-amino protected amino acids are coupled, seriatim, in the desired order to obtain the product. Alternatively, multiple amino acid groups may be coupled by the solution method prior to coupling with the resin supported amino acid sequence. The selection of an appropriate coupling reagent is within the skill of the art. A particularly suitable coupling reagent is N,N$^1$-diisopropyl carbodiimide. Another suitable coupling reagent is N,N$^1$-dicyclohexycarbodiimide.

Each protected amino acid or amino acid sequence is introduced into the solid phase reactor in about a fourfold excess and the coupling is carried out in a medium of dimethylformamide: methylene chloride (1:1) or in dimethylformamide or methylene chloride alone. In cases where incomplete coupling occurred the coupling procedure is repeated before removal of the α-amino protecting group, prior to introduction of the next amino acid to the solid phase reactor. The success of the coupling reaction at each stage of the synthesis is monitored by the ninhydrin reaction as described by E. Kaiser et al., Analyt. Biochem, 34, 595 (1970).

The in vivo activity of the compounds of this invention was established by subjecting (Gly$_3$-Ala)$^1$-Somatostatin, as a representative compound of this invention, to the following standard test procedure: three groups of nine albino male rats were arranged to provide a control group, a group for observation of Somatostatin activity as the standard and a group for the study of the test compound (Gly$_3$-Ala)$^1$-Somatostatin. Nembutal (50 mg/kg) was injected intraperitoneally into each rat. Fifteen minutes later a subcutaneous injection of the test compound, somatostatin (200 μg/kg) and physiological saline was administered separately to each of the three groups of rats. Ten minutes later 0.5 milliliters of arginine (300 mg/ml, pH 7.2) was injected into the rats heart. The rats were decapitated five minutes later and their blood was collected in Trasylol®-EDTA. Aliquot samples were assayed for growth hormone, glucagon and/or insulin. The compound of this invention, selected as representative of the group of compounds disclosed for test pruposes, was employed in two distinct test procedures at the 100 μg/kg and 300 μg/kg dose levels. The results of these test are as follows:

| | Glucagon (picograms/ml) | Insulin μ units/ml | GH (ng/ml) |
|---|---|---|---|
| (Gly$_3$Ala)$^1$-Somatostatin (100 μg/kg) | 0.5 ± 0.1 | 130 ± 14 | |
| Somatostatin | 1.5 ± 0.8 | 202 ± 29 | |
| Saline | 6.4 ± 1.5 | 199 ± 15 | |
| (Gly$_3$-Ala)$^1$-Somatostatin (300 μg/kg) | 1.4 ± 0.7 | 104 ± 10 | 27 ± 7 |
| Somatostatin | 1.6 ± 0.9 | 115 ± 11 | 12 ± 2 |
| Saline | 4.2 ± 0.6 | 165 ± 13 | 133 ± 15 |

Thus, the compounds of this invention (Gly$_3$-Ala)$^1$-Somatostatin and the amides thereof are comparable in activity at the 100 and 300 μg/kg dose levels to somatostatin itself and are effective substitutes for somatostatin in the treatment of diabetes mellitus and acromegaly, even though the heptadecapeptides of this invention contain more amino acid residues than somatostatin.

Administration of the heptadecapeptides of this invention may be by conventional routes common to somatostatin and related polypeptides, under the guidance of a physician, orally or parenterally, in an amount dictated by the extent of the dysfunction as determined by the physician. The compound may be administered alone or in conjuction with conventional pharmaceutically acceptable carriers and adjuvants, in unit dosage form containing from about 2 to about 100 milligrams per kilogram host body weight. Furthermore, the protamine zinc or protamine aluminum adducts present desireable administrable forms of the heptadecapeptide as is conventional in therapy involving the use of polypeptides.

EXAMPLE 1

The preparation of t-butyloxycarbonyl-S-p-methoxybenzyl-L-cysteine Resin A mixture of chloromethylated resin (Bio-Beads S-X1, 200–400 mesh), (1.1 meq/g) (50 g. or 0.055 moles), t-butyloxycarbonyl-S-p-methoxyzenzyl-L-cysteine (18.8 g., or 0.055 mole), triethylamine (6.8 or 0.048 mole) and absolute ethyl alcohol (250 ml.) is refluxed for 48 hours. After being cooled, the reaction mixture is filtered, washed with ethanol and dried under vacuo.

The resin (58 g.) is substituted to the extent of 0.46 mmoles of t-butyloxycarbonyl-S-p-methoxybenzyl-L-cysteine per gram of resin.

EXAMPLE 2 t-Butyloxycarbonyl-glycyl-glycyl-glycyl-L-alanyl-glycyl-S-p-methoxybenzyl-L-cysteinyl-ε-benzyloxy-carbonyl-L-lysyl-L-asparaginyl-L-phenylalanyl-L-phenylalanyl-L-tryptophyl-ε-benzyloxycarbonyl-L-lysyl-O-benzyl-L-threonyl-L-phenylalanyl-O-benzyl-L-threonyl-O-benzyl-L-seryl-S-p-methoxybenzyl-L-cysteine resin The t-butyloxycarbonyl-S-p-methoxybenzyl-L-cysteine resin (29 g.) of Example 1 is placed in a Merrifield vessel of 300 ml. capacity, washed with methanol (200 ml.) twice and methylene chloride (200 ml.) twice, allowing a contact time of at least 3 minutes each. The peptide resin is then subjected to a ninhydrin test following the procedure of E. Kaiser et al., Analytical Biochemistry 34, 595 (1970). It should be negative at this stage.

The deprotection of the α-amino group from t-butyloxycarbonyl-S-p-methoxybenzyl-L-cysteine is carried out as follows: The peptide-resin is treated with a 1:1 solution of trifluoroacetic acid-methylene chloride which contains 5% 1,2-ethanedithiol (three times for 15 minutes each), and put through the following wash cycle:

(a) methylene chloride: (b) dimethylformamide; (c) triethylamine 12.5% in dimethylformamide (three times for 10 minutes each); (d) methanol (two times); (e) methylene chloride (two times). Again, a sample of the peptide resin is subjected to a ninhydrin test. The sample is now strongly positive indicating removal of the α-amino protecting group from the cysteine molecule attached to the resin.

The resin so prepared is then gently shaken with t-butyloxycarbonyl-O-benzyloxy-L-serine (8.4 g., 28.5 moles) in dimethylformamide. 22 ml. of 1 M dicyclohexyl-carbodiimide in dimethylformamide is added in two portions over a period of 30 minutes. Shaking is contined at ambient temperature for a total of 18 hours. The peptide resin is then washed successively with methanol (twice) and methylene chloride (twice). To test for completeness of reaction, the peptide resin is subjected to a ninhydrin agent. It should be negative at this stage.

The removal of the α-amino protecting group at each step is performed as described for the deprotection of the t-butyloxycarbonyl-S-p-methoxybenzyl-L-cysteine resin.

The following amino acid residues are then introduced consecutively (BOC means butyloxycarbonyl): t-BOC-O-benzyl-L-threonine (28.5 mmoles, 28.5 moles DCC), t-BOC-L-phenylalanine (28.5 moles, 28.5 mole DCC), t-BOC-O-benzyl-L-threonine (28.5 moles, 28.5 moles DCC), t-BOC-ε-benzyloxycarbonyl-L-lysine (28.5 moles, 28.5 moles DCC), t-BOC-L-tryptophan (28.5 moles, 28.5 moles DCC), t-BOC-L-phenylalanine (28.5 moles, 28.5 moles DCC), t-BOC-L-phenylalanine (28.5 moles, 28.5 moles DCC), t-BOC-L-asparagine-p-nitrophenyl ester (28.5 moles, 1% acetic acid in DMF (200 ml.)), t-BOC-ε-benzyloxycarbonyl-L-lysine (28.5 moles, 28.5 moles DCC), t-BOC-S-p-methoxy-benzyl-L-cysteine (28.5 moles, 28.5 moles DCC), and t-BOC-L-alanylglycine (28.5 moles, 28.5 moles DCC). Each coupling step is carried out in a medium of dimethylformamide with the exception of asparagine which is used as 1% acetic acid in dimethylformamide.

At this point in the synthesis, the resin which is linked to the polypeptides—t-BOC-L-alanyl-glycyl-S-p-methoxybenzyl-L-cysteinyl-benzyloxycarbonyl-L-lysyl-L-asparaginyl-L-phenylalanyl-L-phenylalanyl-L-tryptophyl-benzyloxycarbonyl-L-lysyl-O-benzyl-ε-threonyl-L-phenylalanyl-O-benzyl-L-threonyl-O-benzyl-L-seryl-S-p-methoxybenzyl-L-cysteine—is removed from the reactor before the deblocking step, dried and weighed. The weight of the resin bearing the tetradecapeptide is now 47 g. 8.0 g. of this intermediate is coupled with t-BOC-glycine (11.4 mmoles, 6 ml. DCC), the pentadecapeptide bound resin is again removed before the deblocking step. The resin is washed, dried in vacuo, and yields 8.1 g. of the protected resin. Again, the synthesis is continued on a 4.0 g. scale and the following amino acid residues are added: t-BOC-glycine(5.7 mmoles, 3.0 ml. DCC), t-BOC-glycine (5.7 mmoles, 3.0 ml. DCC). At this stage the heptadecapeptide bound resin is washed, dried in vacuo, and yields 4.0 g. of the above titled compound.

EXAMPLE 3

Glycyl-glycyl-glycyl-L-alanyl-glycyl-L-cysteinyl-L-lysyl-L-asparaginyl-L-phenylalanyl-L-phenylalanyl-L-tryptophyl-L-lysyl-L-threonyl-L-phenylalanyl-L-threonyl-L-seryl-L-cysteine The above described peptide (4.0 g) in Example 2 is treated in vacuo with liquid hydrogen fluoride (40 ml.) and (12 ml.) at ice bath temperature for 1 hour. The hydrogen fluoride and the anisole are removed as quickly as possible under reduced pressure and the residue washed with ether. The peptide is dissolved in 10% acetic acid (degassed) and separated from the resin by filtration. Lyophilization yields the above titled product as white powder (860 mg.).

Alternatively, the peptide resin product of Example 2 is removed from the resin support by treatment with an amine of the formula

in which $R^{10}$ and $R^{12}$ are methyl or $R^{10}$ is hydrogen and $R^{12}$ is methyl, ethyl, propyl, isopropyl, butyl, secondary butyl, pentyl, or phenethyl followed by removal of any excess of the amine to yield the intermediate

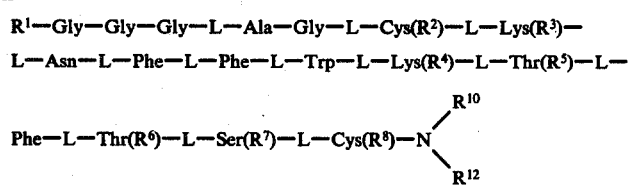

in which the groups $R^1$—$R^{12}$ are defined, supra.

The fully protected intermediate amide is then deprotected with liquid HF in the presence of anisole to yield

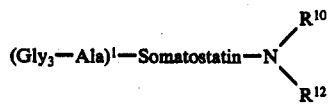

Thus, the protected peptide resin product of Example 2 (4.0 g.) in anhydrous ethylamine (143 ml.) is stirred at room temperature for 18 hours in a glass pressure bottle. The product is filtered, washed with dimethylformamide (three times) and the combined filtrate and washings is concentrated in vacuo to yield the fully protected derivative of (Gly-Ala)$^1$-somatostatin-HHC$_2$H$_5$, which is treated with liquid HF (40 ml.) and anisole (9.3 ml.) in vacuo at ice bath temperature for one hour. The HF is removed so quickly as possible. Degassed water (300 ml. × 2) is added to the residue and extracted with diethyl ether. The combined aqueous layer is lyophilized to yield fully deprotected (Gly$_3$-Ala)$^1$-somatostatin-NHC$_2$H$_5$.

EXAMPLE 4

Cyclization to glycyl-glycyl-glycyl-L-alanyl-glycyl-L-cysteinyl-L-lysyl-L-asparaginyl-L-phenylalanyl-L-phenylalanyl-L-tryptophyl-L-lysyl-L-threonyl-L-phenylalanyl-L-threonyl-L-seryl-L-cysteine cyclic (6→∫) disulfide, triacetate The linear peptide acid (860 mg.) of Example 3 is dissolved in 860 ml. of a degassed ammonium acetate solution which contains 8.6 g. of ammonium acetate and adjusted to pH 7.5 with ammonium hydroxide.

The solution is flushed with nitrogen, and the solution is allowed to stand in air for 96 hours at room temperature. After lyophilization, a white powder (850 mg.) is obtained The amides of Example 3 are readily cyclized under the same conditions.

EXAMPLE 5

Purification of glycyl-glycyl-glycyl-L-alanylglycyl-L-cysteinyl-L-lysyl-L-asparaginyl-L-phenylalanyl-L-phenylalanyl-L-tryptophyl-L-lysyl-L-threonyl-L-phenylalanyl-L-threonyl-L-seryl-L-cysteine cyclic (6→∫) disulfide, triacetate The crude peptide acid (850 mg.) of Example 4 is dissolved in a minimum volume of 2.0 N acetic acid and applied to a Sephadex G-25 (fine) gel filtration column (200 cm. × 2.5 cm.) and eluted with same solvent. Fractions of 9 ml. each are collected. The fractions (72-95) containing the desired peptide are located by ninhydrin spot test and UV analysis (280 mu). After pooling and lyophilization, a white fluffy powder (236 mg.) is obtained.

A partition column of Sephadex G-25 (100 cm. × 2.5 cm.) is prepared by equilibration with low phase and then upper phase of BAW solvent system (n-butanol:acetic acid:water, 4:1:5).

The lyophilized peptide (236 mg.) from above is applied in a minimum volume (10 ml.), of upper phase. Elution with upper phase (4 ml. fractions) affords the desired product which is located by ninhydrin sport test and UV analysis (280 mu). After pooling and lyophilization, a white powder (68 mg.) of the above titled peptide is obtained.

The optical rotation is measured on a Carl Zeiss LEP A-2 photoelectric precision polarimeter, $[\alpha]_D = -41.04$ (c=1.0, 1% acetic acid); amino acid analysis gives the following ratios: Asn (1.1), Thr (2.0); Ser (0.9); Cys (2.2); Ala (1.0); Gly (4.0); Phe (2.9); Lys (2.0); Trp (0.7); Rf (on silica); 0.26 (n-butanol: acetic acid:water, 4:1:5).

Essentially the same purification technique is employed with the amide as is used for the free acid, to obtain the purified amide.

What is claimed is:

1. A compound selected from the group consisting of

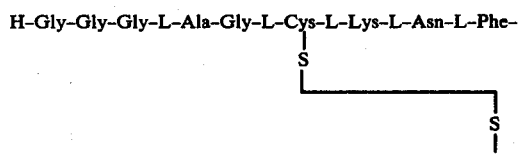

in which R is dimethylamino, alkylamino of 1 to 5 carbon atoms or phenethylamino, the corresponding linear heptadecapeptide, to protamine zinc, protamine aluminum and non-toxic acid addition salts thereof.

2. The heptadecapeptide of claim 1 which is glycyl-glycyl-glycyl-L-alanylglycyl-L-cysteinyl-L-lysyl-L-asparaginyl-L-phenylalanyl-L-phenylalanyl-L-tryptophyl-L-lysyl-L-threonyl-L-phenylalanyl-L-threonyl-L-seryl-L-cysteine ethylamide.

3. The heptadecapeptide of claim 1 which is glycyl-glycyl-glycyl-L-alanylglycyl-L-cysteinyl-L-lysyl-L-asparaginyl-L-phenylalanyl-L-phenylalanyl-L-tryptophyl-L-lysyl-L-threonyl-L-phenylalanyl-L-threonyl-L-seryl-L-cysteine [6-17 disulfide] ethylamide.

* * * * *